United States Patent
Kawata et al.

(10) Patent No.: US 6,528,460 B2
(45) Date of Patent: Mar. 4, 2003

(54) LUBRICANT COMPOSITION

(75) Inventors: Ken Kawata, Kanagawa-ken (JP); Yoshio Fuwa, Aichi-ken (JP); Fumio Ueda, Aichi-ken (JP); Hitoshi Miyata, Aichi-ken (JP); Hirofumi Iisaka, Aichi-ken (JP)

(73) Assignees: Fuji Photo Film Co., Ltd., Tokyo-to (JP); Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 09/880,962

(22) Filed: Jun. 15, 2001

(65) Prior Publication Data

US 2002/0147117 A1 Oct. 10, 2002

(30) Foreign Application Priority Data

Jun. 15, 2000 (JP) ......................... 2000-180303
Jun. 8, 2001 (JP) ......................... 2001-173450

(51) Int. Cl.$^7$ ......................... C10M 133/42
(52) U.S. Cl. ................. 508/258; 508/243; 508/257
(58) Field of Search ................. 508/257, 258

(56) References Cited

U.S. PATENT DOCUMENTS

| | | | |
|---|---|---|---|
| 3,156,689 A | * 11/1964 | Dexter et al. | 544/219 |
| 3,156,690 A | * 11/1964 | Dexter et al. | 544/211 |
| 3,424,683 A | * 1/1969 | Dazzi et al. | 508/258 |
| 3,530,127 A | * 9/1970 | Biland et al. | 508/258 |
| 4,038,197 A | * 7/1977 | Caspari | 508/258 |
| 4,906,751 A | * 3/1990 | Schneider | 508/258 |
| 5,032,301 A | * 7/1991 | Pawloski et al. | 508/257 |
| 5,037,568 A | * 8/1991 | O'Neil et al. | 508/258 |
| 5,198,130 A | * 3/1993 | Schumacher | 508/258 |
| 5,433,873 A | * 7/1995 | Camenzind | 508/258 |
| 5,507,963 A | * 4/1996 | Wolf | 508/258 |

FOREIGN PATENT DOCUMENTS

| | | |
|---|---|---|
| EP | 0 464 991 A2 | 1/1992 |
| GB | 977587 | 12/1964 |
| JP | 2-1436 | 1/1990 |
| JP | 2-79973 | 3/1990 |
| JP | 5-3326 | 1/1993 |
| JP | 8-2582 | 1/1996 |
| WO | 98/55464 | 12/1998 |

OTHER PUBLICATIONS

Janietz et al, Chemical Abstracts, 131:358549f, "Control of mesomorphic structures of 1,3,5–triazines through molecular shape and intramolecular functionalization".

Goldmann et al, *Liquid Crystals*, "New disc-shaped triarylamino–1,3,5–triazines with heteroaromatic central cores", vol. 21, No. 5, pp 619–623 (1996).

European Search Report dated Sep. 26, 2001 in EP 01 164 182 A1.

* cited by examiner

*Primary Examiner*—Ellen M. McAvoy
(74) *Attorney, Agent, or Firm*—Burns, Doane, Swecker & Mathis, LLP

(57) ABSTRACT

It is an object of the present invention to provide a practical lubricant composition excellent in wear resistance, extreme pressure properties and low friction properties for mechanical friction sliding members. The lubricant composition contains, as a major ingredient, a compound of formula (1), preferably a compound of triazine structure:

$$(R-X-)_m-D \quad (1)$$

wherein D is a heterocyclic residue of a 5- to 7-membered cyclic structure positioned at the center of the molecule, or a compound residue of cyclic structure with m radiating side chains; X is a single bond, a group represented by $NR^1$ (wherein $R^1$ is an alkyl group having a carbon number of 1 to 30 or a hydrogen atom), an oxygen atom, a sulfur atom, a carbonyl group, a sulfonyl group, or a combination thereof forming a divalent coupling group; R is an alkyl, alkenyl, alkynyl, aryl or heterocyclic group; and m is an integer from 3 to 11.

6 Claims, No Drawings

LUBRICANT COMPOSITION

CROSS-REFERENCE TO RELATED APPLICATIONS

This application claims the benefit of priority under 35 U.S.C. § 119 to Japanese Application No. 2000-180303, filed Jun. 15, 2000, and Japanese Application No. 2001-173450, filed Jun. 8, 2001, the entire contents of which applications being incorporated herein by reference.

BACKGROUND OF THE INVENTION

1. Field of the Invention

The present invention relates to a lubricant composition which can be supplied to a mechanical friction sliding member, and more particularly to a lubricant composition which is excellent in wear resistance, extreme pressure properties and low friction properties.

2. Description of the Related Art

The use of a liquid-crystalline compound or the like as a lubricant oil or composition has been studied. For example, International Patent Publication No. WO503326/1990 proposes use of a liquid crystal as a lubricant composition as a fluid organic material for a machine member working under varying frictional conditions, where transformation of the liquid crystal between the thermotropic and isotropic phases is utilized. Japanese Patent Publication No. 21436/1990 proposes a chronometer oil mainly composed of a liquid crystal or mixture of liquid crystals, in particular nematic liquid crystal. Japanese Laid-Open Patent Application No.82582/1995 proposes a lubricant composition containing a liquid crystal compound and fluorine-based oil, and Japanese Laid-Open Patent Application No.279973/1998 proposes a lubricant containing a liquid-crystalline compound of sulfur-containing phthalocyanine or metal complex.

In spite of these proposals, however, the techniques are not yet sufficiently developed for use of a single body of liquid-crystalline compound or the like as a lubricant or dissolving a liquid-crystalline compound in a lubricant base oil, in order to produce a lubricant oil or composition containing a practical liquid-crystalline compound or the like, sufficiently excellent in wear resistance, extreme pressure properties and low friction properties. Recently, machine sliding members, in particular, have been required to work at higher temperatures, at higher or lower speeds, and/or at higher loads, as well as becoming smaller and/or lighter. Accordingly, the lubricating conditions for these members are also becoming more severe, needing more practical lubricant of higher wear resistance, extreme pressure properties and low friction properties.

SUMMARY OF THE INVENTION

It is an object of the present invention to provide a practical lubricant composition excellent in wear resistance, extreme pressure properties and low friction properties, for example, for mechanical friction sliding members.

The inventors of the present invention have found, after having extensively studied to solve the problems associated with the above-described conventional techniques, that a compound having a specific structure exhibits excellent properties, in particular low friction coefficient, under severe lubricating conditions, i.e., boundary lubrication or mixed lubrication conditions, reaching the present invention.

According to a first aspect of the invention, provided is a lubricant composition comprising, as a major ingredient, a compound of formula (1):

$$(R-X-)m-D \qquad (1)$$

wherein D is a heterocyclic residue of a 5- to 7-membered cyclic structure positioned at the center of the molecule, or a compound residue of cyclic structure with m radiating side chains; X is a single bond, a group represented by $NR^1$ (wherein $R^1$ is an alkyl group having a carbon number of 1 to 30 or a hydrogen atom), an oxygen atom, a sulfur atom, a carbonyl group, a sulfonyl group, or a combination thereof forming a divalent coupling group; R is an alkyl, alkenyl, alkynyl, aryl or heterocyclic group; and m is an integer from 3 to 11.

In the lubricant composition, each of at least 3 of the m R groups preferably contains a substituent containing a straight or branched alkyl chain having a total carbon number of 8 or more, a straight or branched oligoalkyleneoxy chain having a total carbon number of 4 or more, a straight or branched polyalkyl fluoride chain having a total carbon number of 2 or more, a straight or branched polyalkyl fluoride ether chain having a total carbon number of 2 or more, or a straight or branched organopolysilyl chain.

The formula (1) can be a triazine, preferably represented by formula (2), i.e., D in formula (1) is a 1,3,5-trisubstituted triazine ring:

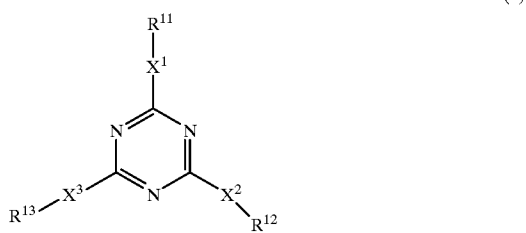

wherein, $X^1$, $X^2$ and $X^3$ are each a single bond, a group represented by $NR^1$ (wherein $R^1$ is an alkyl group having a carbon number of 1 to 30 or a hydrogen atom), an oxygen atom, a sulfur atom, a carbonyl group, a sulfonyl group, or a combination thereof forming a divalent coupling group; and $R^{11}$, $R^{12}$ and $R^{13}$ are each an alkyl, alkenyl, alkinyl, aryl or heterocyclic group. Each of $X^1$, $X^2$ and $X^3$ in formula (2) is preferably an imino group (—NH—).

The composition can contain one or more additives selected from the group consisting of antiwear agents, extreme pressure agents, antioxidants, viscosity index improvers, detergent-dispersants, metal deactivators, corrosion inhibitors, rust inhibitors, antifoamants and combinations thereof.

The composition preferably is composed of a base oil comprising 0.1 to 20% by weight, based on the base oil, of the compound of formula (1), and 80 to 99.9% by weight, based on the base oil, of a mineral and/or synthetic oil.

DETAILED DESCRIPTION OF PREFERRED EMBODIMENTS OF THE INVENTION

1. The Compound of Formula (1)

The compound used as the major ingredient for the lubricant composition of the present invention is a heterocyclic compound shown by the chemical formula (1):

$$(R-X-)m-D \qquad (1)$$

wherein D is a heterocyclic residue of a 5- to 7-membered cyclic structure positioned at the center of the molecule, or a compound residue of cyclic structure with m radiating side chains; X is a single bond, a group represented by $NR^1$ (wherein $R^1$ is an alkyl group having a carbon number of 1 to 30 or a hydrogen atom), an oxygen atom, a sulfur atom, a carbonyl group, a sulfonyl group, or a combination thereof forming a divalent coupling group; R is an alkyl, alkenyl, alkynyl, aryl or heterocyclic group; and m is an integer from 3 to 11.

D in the chemical formula (1) can be a heterocyclic residue of 5- to 7-membered cyclic structure positioned at the center of the molecule, preferably 5- or 6-membered, more preferably 6-membered. Examples of these skeletons are described in Iwanami Rikagaku Jiten, third edition (revised and enlarged), published by Iwanami Shoten, Appendix Chapter 11, Nomenclature of Organic Chemistry, Table 4: Names of Main Heterocyclic Compounds, pp.1606. The heterocyclic rings preferably show aromaticity.

When X in the chemical formula (1) is a single bond, it may be directly bonded by a nitrogen atom with free valence, such as that in a heterocyclic group (e.g., piperidine group). Moreover, it may be bonded by a hetero atom having no free valence, to form an onium salt, e.g., oxysonium, sulfonium or ammonium salt. X in the chemical formula (1) is preferably a sulfur atom or a group represented by the formula $NR^1$, wherein $R^1$ is preferably an alkyl group having a carbon number of 3 or less, or a hydrogen atom. A carbamoyl, sulfamoyl, carboxyl, sulfo, hydroxyamino group or the like may be also used.

When R in the chemical formula (1) is an alkyl group, it has a carbon number of 1 to 30, preferably 2 to 30, more preferably 4 to 30, still more preferably 6 to 30. The alkyl group may be of straight chain or branched. It may have a substituent. The substituents include, for example, a halogen atom, an alkoxy group (e.g., methoxy, ethoxy, methoxyethoxy or phenoxy), a sulfide group (e.g., methylthio, ethylthio or propylthio), an alkyl amino group (e.g., methylamino or propylamino), an acyl group (e.g., acetyl, propanoyl, octanoyl or benzoyl) and an acyloxy group (e.g., acetoxy, pivaloyloxy or benzoyloxy), and a hydroxyl, mercapto, amino, carboxyl, sulfo, carbamoyl, sulfamoyl or ureide group.

When R in the chemical formula (1) is an alkenyl or alkinyl group, it is the same as the alkyl group in carbon number and shape. It may also have the same or similar substituent(s).

When R in the chemical formula (1) is an aryl group, it may be a phenyl, indenyl, α-naphthyl, β-naphthyl, fluorenyl, phenanthrenyl, anthracenyl or pyrenyl group, of which a phenyl or naphthyl group is more preferable. It may also have a substituent, e.g., an alkyl group in addition to those described above as the substituents for the alkyl group. It is preferably substituted with a straight-chain or branched group having a carbon number of 8 or more. The preferable substituents include an alkyl group (e.g., octyl, decyl, hexadecyl or 2-ethylhexyl), alkoxy group (e.g., dodecyloxy or hexadecyloxy), sulfide group (e.g., hexadecylthio) and substituted amino group (e.g., heptadecylamino), and octylcarbamoyl, octanoyl and decylsulfamoyl group. It is preferably substituted with 2 or more substituents, and may also be substituted with a halogen atom, or hydroxyl, cyano, nitro, carboxyl, sulfo group or the like, in addition to the above-described substituents.

When R in the chemical formula (1) is a heterocyclic group, it is, like D in chemical formula (1), preferably a heterocyclic residue of a 5- to 7-membered cyclic structure, more preferably 5- or 6-membered, still more preferably 6-membered. Examples of these skeletons are described in Iwanami Rikagaku Jiten, third edition (revised and enlarged), published by Iwanami Shoten, Appendix Chapter 11, Nomenclature of Organic Chemistry, Table 4: Names of Main Heterocyclic Compounds, pp.1606 and Table 5: Names of Main Condensed Heterocyclic Compounds, pp.1607. It may have a substituent, as is the case with the aryl group. It is preferably substituted with a straight-chain or branched group having a carbon number of 8 or more, as is the case with an aryl group. It is preferably substituted with 2 or more substituents, and may be also substituted with a halogen atom, or hydroxyl, cyano, nitro, carboxyl, sulfo group or the like, in addition to the above-described substituents.

Preferably, each of at least 3 of the m R groups contains a substituent containing a straight or branched alkyl chain having a total carbon number of 8 or more, a straight or branched oligoalkyleneoxy chain having a total carbon number of 4 or more, a straight or branched polyalkyl fluoride chain having a total carbon number of 2 or more, a straight or branched polyalkyl fluoride ether chain having a total carbon number of 2 or more, or a straight or branched organopolysilyl chain. Preferable examples of the straight alkyl chains having a total carbon number of 8 or more include n-octyl, n-octyloxy, n-octylthio, n-octylamino, n-nonyl, n-nonyloxy, n-decyl, n-decyloxy, n-undecyl, n-undecyloxy, n-dodecyl, n-dodecyloxy, n-dodecylthio, n-dodecylamino, n-pentadecyl, n-pentadecyloxy, n-hexadecyl, n-hexadecyloxy, n-hexadecylthio, and n-hexadecylamino groups. The branched alkyl chains having a total carbon number of 8 or more include 2-ethylhexyl, 2-ethylhexyloxy, 2-ethylhexylthio, 2-ethylhexylamino, 2-hexyldecyl, 2-hexyldecylthio, 2-hexyldecylamino, 3,7,11,15-tetramethylhexadecyl, 3,7,11,15-tetramethylhexadecyloxy, 3,7,11,15-tetramethylhexadecylthio, and 3,7,11,15-tetramethylhexadecylamino groups. The straight or branched oligoalkyleneoxy chains having a total carbon number of 4 or more include diethyleneoxy, triethyleneoxy, tetraethyleneoxy, dipropyleneoxy, and hexyloxyethyleneoxyethyleneoxy groups.

The preferable examples of the straight or branched polyalkyl fluoride chains having a total carbon number of 2 or more include pentadecylfluoroheptyl, pentadecylfluoroheptylcarbonyloxy, heptadecylfluorooctyl, and pentadecylfluorooctylsulfonyl groups. The straight or branched polyalkyl fluoride ether chains having a total carbon number of 2 or more include the side-chain type, e.g., isopropyleneoxide-based, and straight-chain type, e.g., those of methylene oxide/ethylene oxide mixture and propylene oxide-based type.

The straight or branched organopolysilyl chains include those with the silicon-containing group in the side chain of a long-chain substituent, e.g., poly(p-trimethylsilylstyrene) and poly(1-trimethylsilyl-1-propyne); and those with silicon in the main chain in a long-chain substituent, the latter being more preferable. The examples with silicon in the main chain include straight-chain, branched, cyclic or polycyclic long-chain substituents having the repeating unit of the structure shown by the following formula:

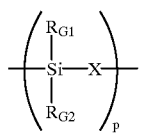

wherein $R_{G1}$ and $R_{G2}$ are each a substituent, and may be bound to each other to form a ring structure; X is oxygen, nitrogen, alkylene, phenylene, silicon, metallic atom, or a group composed of two or more of the above; and p is an integer of 1 to 30.

The straight or branched organopolysilyl chains include polysiloxane, polysilazane, polysilylmethylene, polysilylphenylene, polysilane and polymetallosiloxane. X is preferably oxygen or a group in which oxygen is bound to an alkylene group, more preferably oxygen. $R_{G1}$ and $R_{G2}$ are each the same as the substituent R in each of the general formulae, preferably an alkyl group.

D in the chemical formula (1) is preferably a 1,3,5-trisubstituted triazine ring, i.e., a compound shown by the following chemical formula (2), and the compound shown by the chemical formula (2) is more preferably a melamine-based one substituted with an amino group which is substituted with an aromatic ring:

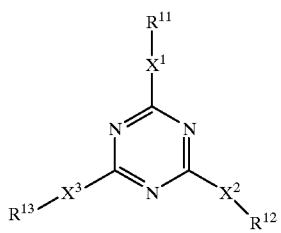

(2)

wherein, $X^1$, $X^2$ and $X^3$ are each a single bond, a group represented by $NR^1$ (wherein $R^1$ is an alkyl group having a carbon number of 1 to 30 or a hydrogen atom), an oxygen atom, a sulfur atom, a carbonyl group, a sulfonyl group, or a combination thereof forming a divalent coupling group; and $R^{11}$, $R^{12}$ and $R^{13}$ are each an alkyl, alkenyl, alkinyl, aryl or heterocyclic group.

When $X^1$, $X^2$ or $X^3$ in the chemical formula (2) is a single bond, it may be directly bonded by a nitrogen atom with free valence, such as that in a heterocyclic group (e.g., a piperidine group). Moreover, it may be bonded by a hetero atom having no free valence, to form an onium salt, e.g., oxysonium, sulfonium or ammonium salt. $X^1$, $X^2$ or $X^3$ in the chemical formula (2), when not a single bond, is preferably a group represented by the formula $NR^1$ (wherein $R^1$ is an alkyl group having a carbon number of 1 to 30 or a hydrogen atom), an oxygen atom, a sulfur atom, a carbonyl group, a sulfonyl group, or a combination thereof forming a divalent coupling group, e.g., an oxycarbonyl, aminocarbonyl, ureylene, oxysulfonyl or sulfamoyl group. It is preferably a sulfur atom or a group shown by the formula $NR^1$, wherein $R^1$ is preferably an alkyl group having a carbon number of 3 or less, or a hydrogen atom, of which imino group (—NH—) is more preferable.

$R^{11}$, $R^{12}$ or $R^{13}$ in the chemical formula (2) is an alkyl group having a carbon number of 1 to 30, preferably 2 to 30, more preferably 4 to 30, still more preferably 6 to 30. The alkyl group may be a straight chain or branched. It may have a substituent. The substituents include, for example, a halogen atom, an alkoxy group (e.g., methoxy, ethoxy, methoxyethoxy or phenoxy), a sulfide group (e.g., methylthio, ethylthio or propylthio), an alkyl amino group (e.g., methylamino or propylamino), an acyl group (e.g., acetyl, propanoyl, octanoyl or benzoyl) and an acyloxy group (e.g., acetoxy, pivaloyloxy or benzoyloxy), and a hydroxyl, mercapto, amino, carboxyl, sulfo, carbamoyl, sulfamoyl or ureide group.

When $R^{11}$, $R^{12}$ or $R^{13}$ in the chemical formula (2) is an alkenyl or alkinyl group, it is the same as the alkyl group in carbon number and shape. It may also have the same or similar substituent.

When $R^{11}$, $R^{12}$ or $R^{13}$ in the chemical formula (2) is an aryl group, it may be phenyl, indenyl, α-naphthyl, β-naphthyl, fluorenyl, phenanthrenyl, anthracenyl or pyrenyl group, of which phenyl or naphthyl group is more preferable. It is preferably substituted with a straight-chain or branched group having a carbon number of 8 or more. The preferable substituents include an alkyl group (e.g., octyl, decyl, hexadecyl or 2-ethylhexyl), alkoxy group (e.g., dodecyloxy, hexadecyloxy, 2-hexyldecyloxy or hexyloxyethyleneoxyethyleneoxy), sulfide group (e.g., hexadecylthio) and substituted amino group (e.g., heptadecylamino), and octylcarbamoyl, octanoyl and decylsulfamoyl group. It is preferably substituted with 2 or more substituents, and may be also substituted with a halogen atom, or hydroxyl, cyano, nitro, carboxyl, sulfo group or the like, in addition to the above-described substituents.

When $R^{11}$, $R^{12}$ or $R^{13}$ in the chemical formula (2) is a heterocyclic group, it is, like D in the chemical formula (1), preferably a heterocyclic residue of 5- to 7-membered cyclic structure, more preferably 5- or 6-membered, still more preferably 6-membered. Examples of these skeletons are described in Iwanami Rikagaku Jiten, third edition (revised and enlarged), published by Iwanami Shoten, Appendix Chapter 11, Nomenclature of Organic Chemistry, Table 4: Names of Main Heterocyclic Compounds, pp.1606 and Table 5: Names of Main Condensed Heterocyclic Compounds, pp.1607. It is preferably substituted with a straight-chain or branched group having a carbon number of 8 or more, as is the case with aryl group. It is preferably substituted with 2 or more substituents, and may be also substituted with a halogen atom, or hydroxyl, cyano, nitro, carboxyl, sulfo group or the like, in addition to the above-described substituents. It is more preferable that each of $R^{11}$, $R^{12}$ and $R^{13}$ in the chemical formula (2) contains the substituent containing a straight or branched alkyl chain having a total carbon number of 8 or more, straight or branched oligoalkyleneoxy chain having a total carbon number of 4 or more, straight or branched polyalkyl fluoride chain having a total carbon number of 2 or more, straight or branched polyalkyl fluoride ether chain having a total carbon number of 2 or more, or straight or branched organopolysilyl chain. $R^{11}$, $R^{12}$ or $R^{13}$ in the chemical formula (2) is more preferably phenyl group substituted by a group containing a straight-chain or branched alkyl residue having a carbon number of 8 or more.

The lubricating function of the compound having a triazine structure as the main ingredient for the lubricant composition of the present invention is not well understood, but the inventors of the present invention consider that the lubricating characteristics, e.g., low friction coefficient, are obtained by the effect of adsorption of the triazine structure, in particular melamine structure, on a sliding member (metallic) and interfacial activity or orientation effect of the triazine structure itself. Therefore, preferable compounds of triazine structure are those having a disk-shaped structure, because they are flat and can provide a laminated configuration. Liquid-crystalline compounds are also preferable. These preferable compounds include a group of compounds known as discotic liquid crystals.

The heterocyclic compound, shown by chemical formula (1), for the lubricant composition of the present invention can be produced by various methods. The starting materials and production method are not limited. Most of the compounds of triazine structure shown by the chemical formula (2) can be easily synthesized from inexpensive cyanuric chloride. They are useful as bases for lubricant compositions, because of their compatibility with normally used mineral oils, synthetic oils and additives for lubricants.

Those preferably used are practical liquids at normal temperature and pressure. They can be used either individually, or in combination to make the mixture practical.
The compounds useful for the lubricant composition of the present invention include, but not limited to, those listed below:
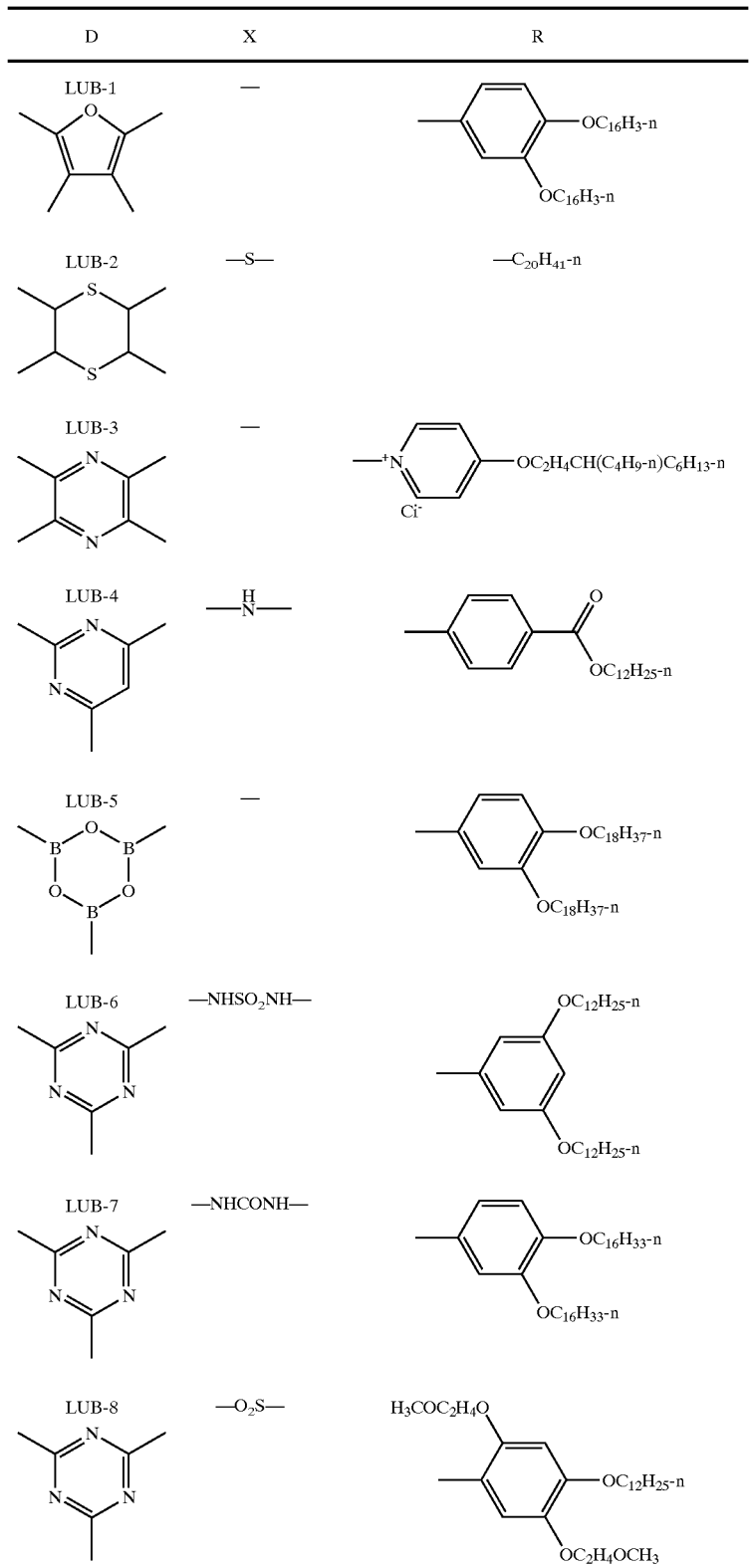

-continued

| D | X | R |
|---|---|---|
| LUB-9 (triazine with 3 methyls) | — | N-methyl phthalimide with two OC$_{14}$H$_{29}$-n groups |
| LUB-10 (triazine with 2 methyls) | —NHO— | phenyl with two OC$_{16}$H$_{33}$-n groups |
| LUB-11 (triazine with 2 methyls) | — | ethynyl-phenyl with two SC$_{15}$H$_{31}$-n groups |
| LUB-12 (triazine with 2 methyls) | — | pyrimidine-N(C$_{16}$H$_{33}$-n)$_2$ |
| LUB-13 (triazine with 2 methyls) | —S— | CH=CH-phenyl with two OC$_{12}$H$_{25}$-n groups |
| LUB-14 (triazine with 2 methyls) | —O— | —CH$_2$—phenyl with two OC$_{18}$H$_{37}$-n groups |
| LUB-15 (triazine with 2 methyls) | —N(CH$_3$)— | phenyl with three OC$_{10}$H$_{21}$-n groups |
| LUB-16 (triazine with 2 methyls) | —NH— | phenyl with two OC$_2$H$_4$CH(C$_4$H$_9$-n)C$_{10}$H$_{21}$-n groups |

-continued

| D | X | R |
|---|---|---|
| LUB-17 triazine | —NH— | 2-methyl-4-(n-C12H25COC4H8O), phenyl with OC4H8COC12H25-n |
| LUB-18 triazine | —NH— | methylphenyl with (OC2H4)2—OC12H25-n and (OC2H4)2—OC12H25-n |
| LUB-19 triazine | —NH— | methylphenyl with three OC12H25-n groups |
| LUB-20 triazine | —NH— | methylphenyl with two OC12H25-n groups |
| LUB-21 triazine | —NH— | 4,5-dimethylphenyl with OC16H33-n and OC2H4OC2H4OC2H5 |
| LUB-22 triazine | —NH— | 2-methylbenzothiazole with OC16H33-n and OC16H33-n |
| LUB-23 triazine | —NH— | mixture of: methylphenyl with OC12H25-n and OC2H4Oc2H5; and dimethylphenyl with OC12H25-n |
| LUB-24 triazine | | N-methylisoindole with SC18H37-n and SC18H37-n |

-continued

| D | X | R |
|---|---|---|
| LUB-25 (2,4,6-trimethyl-1,3,5-triazine) | —NH— | 2-methyl-5-[N,N-di(n-C$_{12}$H$_{25}$)amino]-1,3,4-thiadiazole |
| LUB-26 (2,4,6-trimethyl-1,3,5-triazine) | —NH— | 4-methyl-phenyl with 1,2-bis[OCH$_2$CH(C$_6$H$_{13}$-n)C$_8$H$_{17}$-n] |
| LUB-27 (2,4,6-trimethyl-1,3,5-triazine) | —NH— | 4-methyl-phenyl with 1,2-bis[OCH$_2$CH(C$_8$H$_{17}$-n)C$_{10}$H$_{21}$-n] |
| LUB-28 (2,4,6-trimethyl-1,3,5-triazine) | —NH— | 4-methyl-phenyl with 1,2-bis[(OC$_2$H$_4$)$_2$—OC$_6$H$_{13}$-n] |
| LUB-29 (2,4,6-trimethyl-1,3,5-triazine) | —NH— | 4-methyl-phenyl with 1,2-bis[(OC$_2$H$_4$)$_4$—OC$_8$H$_{17}$-n] |
| LUB-30 (2,4,6-trimethyl-1,3,5-triazine) | —NH— | 4-methyl-phenyl with 1,2-bis[O(C$_2$H$_4$CHMeCH$_2$)$_4$H] |
| LUB-31 (2,4,6-trimethyl-1,3,5-triazine) | —NH— | 4-methyl-phenyl with 1,2-bis[OCH$_2$CH$_2$N(C$_3$H$_7$-n)NSO$_2$C$_8$F$_{17}$-n] |
| LUB-32 (2,4,6-trimethyl-1,3,5-triazine) | —NH— | 3-[OCH$_2$CH$_2$N(C$_3$H$_7$-n)NSO$_2$C$_8$F$_{17}$-n]-phenyl |

-continued

| D | X | R |
|---|---|---|
| LUB-33 triazine | —NH— | phenyl with O(CF$_2$CF$_2$)$_4$—O(CF$_2$)$_7$CF$_3$ and O(CF$_2$CF$_2$)$_4$—O(CF$_2$)$_7$CF$_3$ |
| LUB-34 triazine | —NH— | phenyl with O(SiMe$_2$O)$_8$(C$_2$H$_4$)$_4$OCH$_3$ and O(SiMe$_2$O)$_8$(C$_2$H$_4$)$_4$OCH$_3$ |
| LUB-35 triazine | —NH— and —S— | phenyl with O(C$_2$H$_4$CHMeCH$_2$)$_4$H and O(C$_2$H$_4$CHMeCH$_2$)$_4$H; phenyl with S(C$_2$H$_4$CHMeCH$_2$)$_4$H and S(C$_2$H$_4$CHMeCH$_2$)$_4$H (1..2) |

2. Lubricant Composition

The compound of chemical formula (1) for the lubricant composition of the present invention can be used by itself as the base oil for the composition. However, it is normally used in combination with a mineral or synthetic oil to form the base oil.

The mineral or synthetic oil which can be used for the mixed base oil is not limited, and any one which is normally used as a lubricant base oil can be used. In other words, it may be a mineral oil, synthetic oil or a mixture thereof.

The mineral oils useful for the present invention include lubricant stocks, obtained by atmospheric or vacuum distillation of crude, which are treated by various processes, e.g., raffinate from solvent extraction with an aromatic extractant such as phenol, furfural and N-methyl pyrrolidone; hydrotreated oil obtained by treating lubricant stocks with hydrogen under hydrotreatment conditions in the presence of a hydrotreatment catalyst, such as cobalt- or molybdenum-based one supported by a silica-alumina carrier; hydrocracked oil obtained by treating lubricant stocks with hydrogen under severer hydrocracking conditions; isomerate obtained by isomerizing wax with hydrogen under isomerization conditions in the presence of an isomerization catalyst; and those lubricant fractions obtained by a combination of solvent refining, hydrotreatment, hydrocracking or isomerizatrion. The particularly suitable mineral oils are those of high viscosity index, obtained by hydrocracking or isomerization. Any process described above can be optionally combined with dewaxing, hydrofinishing, clay treatment or the like in a normal manner. More specifically, the mineral oils for the present invention include light, medium and heavy neutral oils, and bright stocks. They can be mixed with one another, to satisfy the requirements of the present invention.

The examples of synthetic base oils useful for the present invention include poly-α-olefin, α-olefin oligomer, polybutene, alkylbenzene, polyol ester, dibasic acid ester, polyoxyalkylene glycol, polyoxyalkylene glycol ether, and silicone oil.

These base oils may be used either individually or in combination. A mineral oil may be combined with a synthetic oil. They may be used to form a mixed base oil for the lubricant composition of the present invention. The base oil for the present invention generally has a kinematic viscosity of 2 to 20 mm$^2$/s at 100° C., preferably 3 to 15 mm$^2$/s. The selected mixed base oil has an optimum kinematic viscosity suitable for the lubricating conditions for a mechanical friction sliding member for which the lubricant composition of the present invention is used.

The lubricant composition of the present invention comprises a base oil composed of 0.1 to 20% by weight, based on the whole base oil, of the compound of triazine structure represented by the chemical formula (2) and 80 to 99.9% by weight of the normal base oil, i.e., a mineral and/or synthetic oil. The base oil is preferably composed of 0.1 to 10% by weight, more preferably 0.1 to 1% by weight of the compound of triazine structure. However, the compound of triazine structure by itself can be used as a base oil for lubricant compositions, as described earlier, frequently more effective when used alone, giving a low friction coefficient in a wide temperature range even under severe lubricating conditions and, at the same time, exhibiting an excellent effect for resistance to wear.

The lubricant composition of the present invention contains, as the main ingredient, the compound represented by chemical formula (1), and may be incorporated with various additives being used for lubricant oils (e.g., bearing oil, gear oil and transmission oil) to secure practical performance for various specific purposes and as required, within limits not harmful to the object of the present invention. These additives include antiwear agents, extreme pressure agents, antioxidants, viscosity index improvers, detergent-dispersants, metal deactivators, corrosion inhibitors, rust inhibitors and antifoamants.

The lubricant composition of the present invention has the advantages of a low friction coefficient, and high wear resistance and extreme pressure properties under severe lubricating conditions. It can be serviceable even at low temperature and practical, i.e., keeping the liquid state even at −40° C., by forming an optimum mixture of the compounds of triazine structure represented by the chemical formula (1), preferably represented by the chemical formula (2).

The above advantages allow the lubricant composition of the present invention to be serviceable under severe lubricating conditions, which would break the film of the conventional lubricating oil or grease, without causing seizure, to keep its wear resistance and low friction coefficient, and hence to suitably work as an energy-saving type lubricant for bearing and gears operating under severe lubricating conditions. The seizure-free serviceability of the lubricant composition under severe lubricating conditions makes the sliding member it lubricates more reliable and smaller.

The present invention is described more concretely by the following examples, which by no means limit the present invention.

EXAMPLES

The lubricant compositions prepared in the following examples and comparative examples were evaluated by the following procedures:
1. Evaluation and Measurement by a Reciprocating Type (SRV) Friction/Wear Tester Friction coefficient and wear resistance were evaluated by the friction/wear tests conducted under the following conditions using a reciprocating type (SRV) friction/wear tester. The wear resistance was also evaluated by measuring depth of wear-caused scars by surface roughness meter.
Test Conditions
Specimen (Friction material): SUJ-2
Plate: 24 mm in diameter, 7 mm thick
Cylinder: 15 mm in diameter, 22 mm long
Temperature: 100° C.
Load: 50 and 400 N
Amplitude: 1.0 mm
Frequency: 50 Hz
Testing period: for 2 min. after the start of testing
2. Compound of Triazine Structure and Lubricant Composition Examples 1 to 3

Each of LUB-20, LUB-26 and LUB-28 was used as the compound of triazine structure and as the sole component of the lubricant, to evaluate its characteristics by the friction/wear tests using a reciprocating type (SRV) friction/wear tester. The results are given in Table 1. It had a low friction coefficient at both low (50 N) and high (400 N) loads, and a wear-caused scar depth of 0.0 $\mu$m, showing good friction and wear characteristics.

Comparative Examples 1 to 7

Comparative Examples 1 to 3 prepared lubricants, each composed only of a friction modifier, as shown in Table 1, normally used for lubricant oil compositions. Each lubricant was tested by a reciprocating type (SRV) friction/wear tester in the same manner as in Example 1. The results are given in Table 1.

Comparative Examples 4 to 7 prepared lubricants, each composed only of a lubricant base oil, as shown in Table 1, normally used for lubricant oil compositions. Each lubricant was tested by a reciprocating type (SRV) friction/wear tester at a low load (50N) in the same manner as in Example 1. The results are also given in Table 1.

TABLE 1

|  | EXAMPLE 1 | EXAMPLE 2 | EXAMPLE 3 | COMPARATIVE EXAMPLE 1 | COMPARATIVE EXAMPLE 2 | COMPARATIVE EXAMPLE 3 | COMPARATIVE EXAMPLE 4 | COMPARATIVE EXAMPLE 5 | COMPARATIVE EXAMPLE 6 | COMPARATIVE EXAMPLE 7 |
|---|---|---|---|---|---|---|---|---|---|---|
| Compound of triazine structure, |  |  |  |  |  |  |  |  |  |  |
| LUB-20, % by weight | 100 | — | — | — | — | — | — | — | — | — |
| LUB-26, % by weight | — | 100 | — | — | — | — | — | — | — | — |
| LUB-28, % by weight | — | — | 100 | — | — | — | — | — | — | — |
| Friction modifier, % by weight |  |  |  |  |  |  |  |  |  |  |
| Sorbitan monooleate | — | — | — | 100 | — | — | — | — | — | — |
| Acid phosphate ester *1 | — | — | — | — | 100 | — | — | — | — | — |
| Alkanol amine *2 | — | — | — | — | — | 100 | — | — | — | — |
| Lubricant base oil, % by weight |  |  |  |  |  |  |  |  |  |  |
| Pentaerythritol ester *3 | — | — | — | — | — | — | 100 | — | — | — |
| Alkyl benzene *4 | — | — | — | — | — | — | — | 100 | — | — |
| Naphthene-based mineral oil | — | — | — | — | — | — | — | — | 100 | — |

TABLE 1-continued

|  | EXAMPLE 1 | EXAMPLE 2 | EXAMPLE 3 | COMPARATIVE EXAMPLE 1 | COMPARATIVE EXAMPLE 2 | COMPARATIVE EXAMPLE 3 | COMPARATIVE EXAMPLE 4 | COMPARATIVE EXAMPLE 5 | COMPARATIVE EXAMPLE 6 | COMPARATIVE EXAMPLE 7 |
|---|---|---|---|---|---|---|---|---|---|---|
| Paraffin-based mineral oil | — | — | — | — | — | — | — | — | — | 100 |
| SRV friction/wear test @ 50 N, 100° C. | | | | | | | | | | |
| Friction coefficient | 0.06 | 0.05 | 0.08 | 0.13 | 0.14 | 0.16 | 0.21 | 0.22 | 0.25 | 0.22 |
| Wear-caused scar depth ($\mu$m) | 0.0 | 0.0 | 0.0 | 0.1 | 0.0 | 0.8 | 0.7 | 0.6 | 0.8 | 0.7 |
| SRV friction/wear test @ 400 N, 100° C. | | | | | | | | | | |
| Friction coefficient | 0.04 | 0.04 | 0.05 | 0.08 | 0.10 | 0.12 | — | — | — | — |
| Wear-caused scar depth ($\mu$m) | 0.0 | 0.0 | 0.0 | 0.1 | 0.0 | 1.3 | — | — | — | — |

*1 Oleyl acid phosphate
*2 Dodecylamine of diethanol
*3 Hexanoate ester of pentaerythritol
*4 Alkyl benzene whose alkyl group has a carbon number of 10

It is confirmed, by comparing the results of Examples 1 to 3 with those of the Comparative Examples, that use of a compound of triazine structure as the main ingredient for a base oil gives a practical lubricant composition excellent in wear resistance and low in friction coefficient even under a high load condition.

The present invention provides a practical lubricant composition, showing excellent wear resistance, extreme pressure and low friction coefficient characteristics on a mechanical friction member. The lubricant composition of the present invention is serviceable under severe lubricating conditions, which would break the film of the conventional lubricating oil or grease, without causing seizure, to keep its wear resistance and low friction coefficient, and hence suitably works as an energy-saving type lubricant for bearing and gears operating under severe lubricating conditions. The seizure-free serviceability of the lubricant composition under severe lubricating conditions makes the sliding member it lubricates more reliable and smaller.

What is claimed is:

1. A lubricant composition comprising a compound of formula (2):

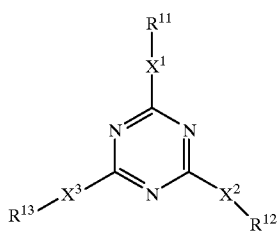

(2)

wherein each of $X^1$, $X^2$ and $X^3$ in formula (2) is an imino group (—NH—), and wherein $R^{11}$, $R^{12}$ and $R^{13}$ are each an aryl group substituted with a straight-chain or branched group having a carbon number of 8 or more.

2. The lubricant composition according to claim 1, further comprising one or more additives selected from the group consisting of antiwear agents, extreme pressure agents, antioxidants, viscosity index improvers, detergent-dispersants, metal deactivators, corrosion inhibitors, rust inhibitors, antifoamants and combinations thereof.

3. The lubricant composition according to claim 1, wherein the composition comprises a base oil comprising 0.1 to 20% by weight, based on the base oil, of the compound of formula (2), and 80 to 99.9% by weight, based on the base oil, of a mineral and/or synthetic oil.

4. The lubricant composition according to claim 3, further comprising one or more additives selected from the group consisting of antiwear agents, extreme pressure agents, antioxidants, viscosity index improvers, detergent-dispersants, metal deactivators, corrosion inhibitors, rust inhibitors, antifoamants and combinations thereof.

5. The lubricant composition according to claim 1, wherein said straight-chain or branched group is selected from the group consisting of an alkyl group, an alkoxy group, a sulfide group, a substituted amino group, an octyl-carbamoyl group, an octanoyl group and a decylsulfamoyl group.

6. The lubricant composition according to claim 5, wherein at least one of the aryl groups is substituted with 2 or more of the straight-chain or branched groups.

* * * * *